United States Patent [19]
Bell et al.

[11] Patent Number: 5,465,731
[45] Date of Patent: Nov. 14, 1995

[54] SPECIMEN RETRIEVAL POUCH AND METHOD FOR USE

[75] Inventors: Mace Bell, Rowayton; Vinod Nagori, Trumbull; Darren E. Zinner, Norwalk, all of Conn.

[73] Assignee: United States Surgical Corporation, Norwalk, Conn.

[21] Appl. No.: 133,547

[22] Filed: Oct. 7, 1993

Related U.S. Application Data

[63] Continuation-in-part of Ser. No. 906,794, Jun. 30, 1992, abandoned.

[51] Int. Cl.$^6$ .................................................. A61B 10/00
[52] U.S. Cl. .................................................. 128/749; 600/37
[58] Field of Search .................................. 128/749, 751, 128/849–851, DIG. 24; 600/37; 604/22, 27, 28

[56] References Cited

U.S. PATENT DOCUMENTS

| | | |
|---|---|---|
| 30,471 | 10/1860 | Dudley . |
| 156,477 | 11/1874 | Bradford . |
| 1,609,014 | 11/1926 | Dowd . |
| 3,800,781 | 4/1974 | Zalucki . |
| 4,557,255 | 12/1985 | Goodman . |
| 4,744,363 | 5/1988 | Hasson . |
| 4,790,812 | 12/1988 | Hawkins, Jr. et al. . |
| 4,927,427 | 5/1990 | Kriauciunas et al. . |
| 4,997,435 | 3/1991 | Demeter . |
| 5,037,379 | 8/1991 | Clayman et al. . |
| 5,074,867 | 12/1991 | Wilk . |
| 5,084,054 | 1/1992 | Bencini et al. . |
| 5,143,082 | 9/1992 | Kindberg et al. . |
| 5,147,371 | 9/1992 | Washington et al. . |
| 5,176,687 | 1/1993 | Hasson et al. . |
| 5,190,542 | 3/1993 | Nakao et al. . |
| 5,190,555 | 3/1993 | Wetter et al. . |
| 5,192,284 | 3/1993 | Pleatman ............................ 606/127 X |
| 5,192,286 | 3/1993 | Phan et al. ............................ 606/127 |
| 5,201,740 | 4/1993 | Nakao et al. . |
| 5,215,521 | 6/1993 | Cochran et al. . |
| 5,234,439 | 8/1993 | Wilk et al. . |
| 5,279,539 | 1/1994 | Bohan et al. . |
| 5,312,416 | 5/1994 | Spaeth et al. . |
| 5,341,815 | 8/1994 | Cofone et al. . |

FOREIGN PATENT DOCUMENTS

| | | |
|---|---|---|
| 1272412 | 8/1961 | France . |
| 25796 | 8/1883 | Germany . |
| 8435489 | 12/1984 | Germany . |
| 3542667 | 6/1986 | Germany . |

OTHER PUBLICATIONS

"Operative Pelviscopy–Endoscopical Ligatures Using the Loop–ligation–Endo–Loop–" by K. Semm, Kiel/W. Germany 1990.

Davol Rubber Company Catalogue, p. 24, 1959.

"Gallbladder Extraction" page from publication describing Endopouch™ retrieval bag, 1991.

"Introducing the Pleatman Sac" advertisement from *Surgical Laparoscopy & Endoscopy*, vol. 2, No. 1, Mar. 1992.

Endopouch™ Brochure, Ethicon, 1992.

Endobag™ Brochure, Dexide, 1992.

Kent III R. B. et al., *Homostasis of the Gallbladder Fossa During Laparoscopic Cholecystectomy*; Surg Laparoscopy & Endoscopy 1991, 1(2):104–105.

Kent III R. B. et al., *Laparoscopic Retrieval of Spilled Stones*; Surg Laparoscopy & Endoscopy 1992; 2(2):152–153.

*Primary Examiner*—Lee S. Cohen
*Assistant Examiner*—Samuel Gilbert

[57] ABSTRACT

A specimen removal pouch and applicator includes a pouch fabricated from a flexible membrane, a drawstring thread forming a running noose disposed circumferentially round the end of the pouch, an endoscopic tubular portion, and a pusher rod having an aperture for permitting the passage therethrough of a single thread. When the drawstring thread is pulled, the knot is stopped at the aperture and the noose is closed, thereby closing the mouth of the pouch. The pouch is detached from the apparatus.

22 Claims, 16 Drawing Sheets

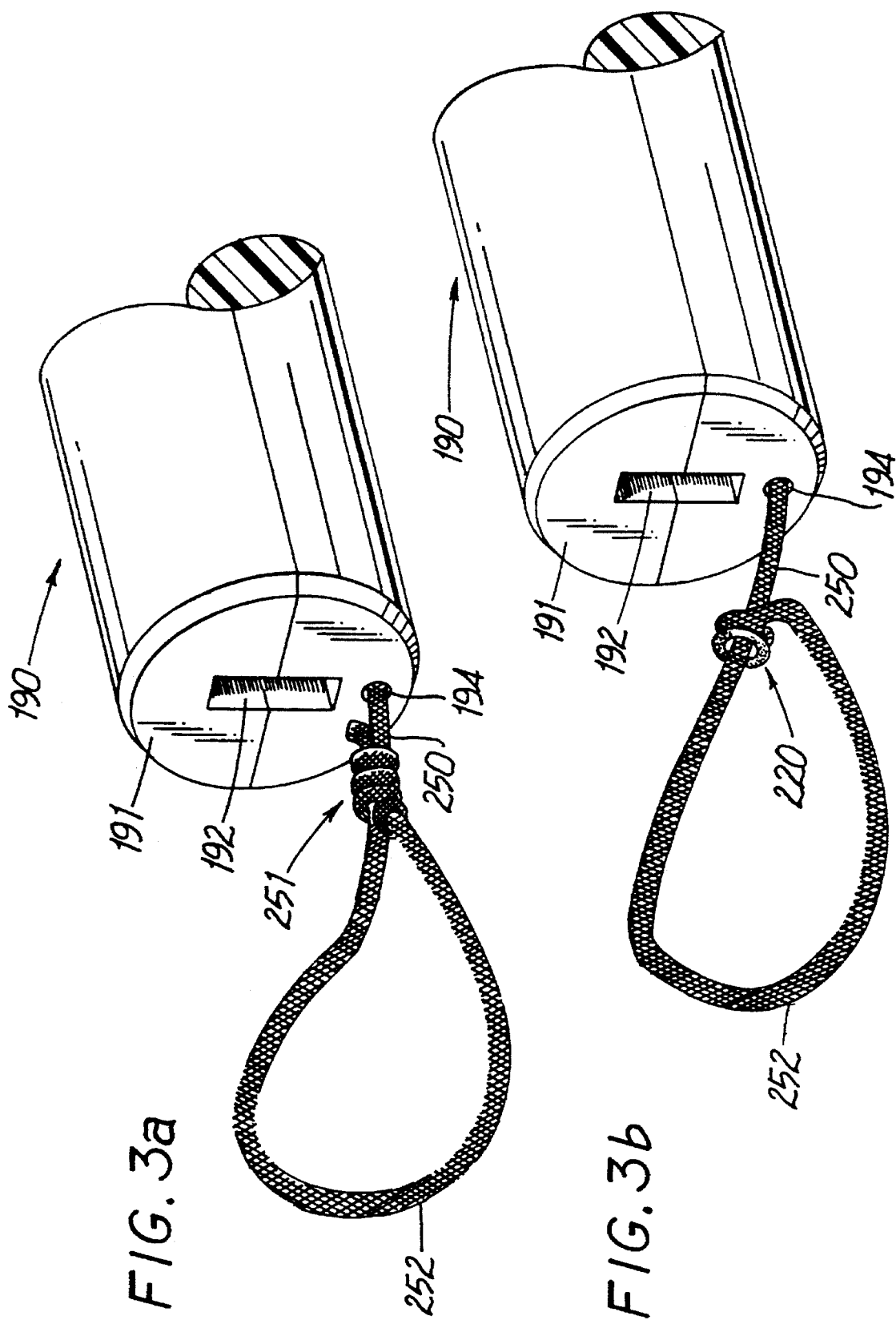

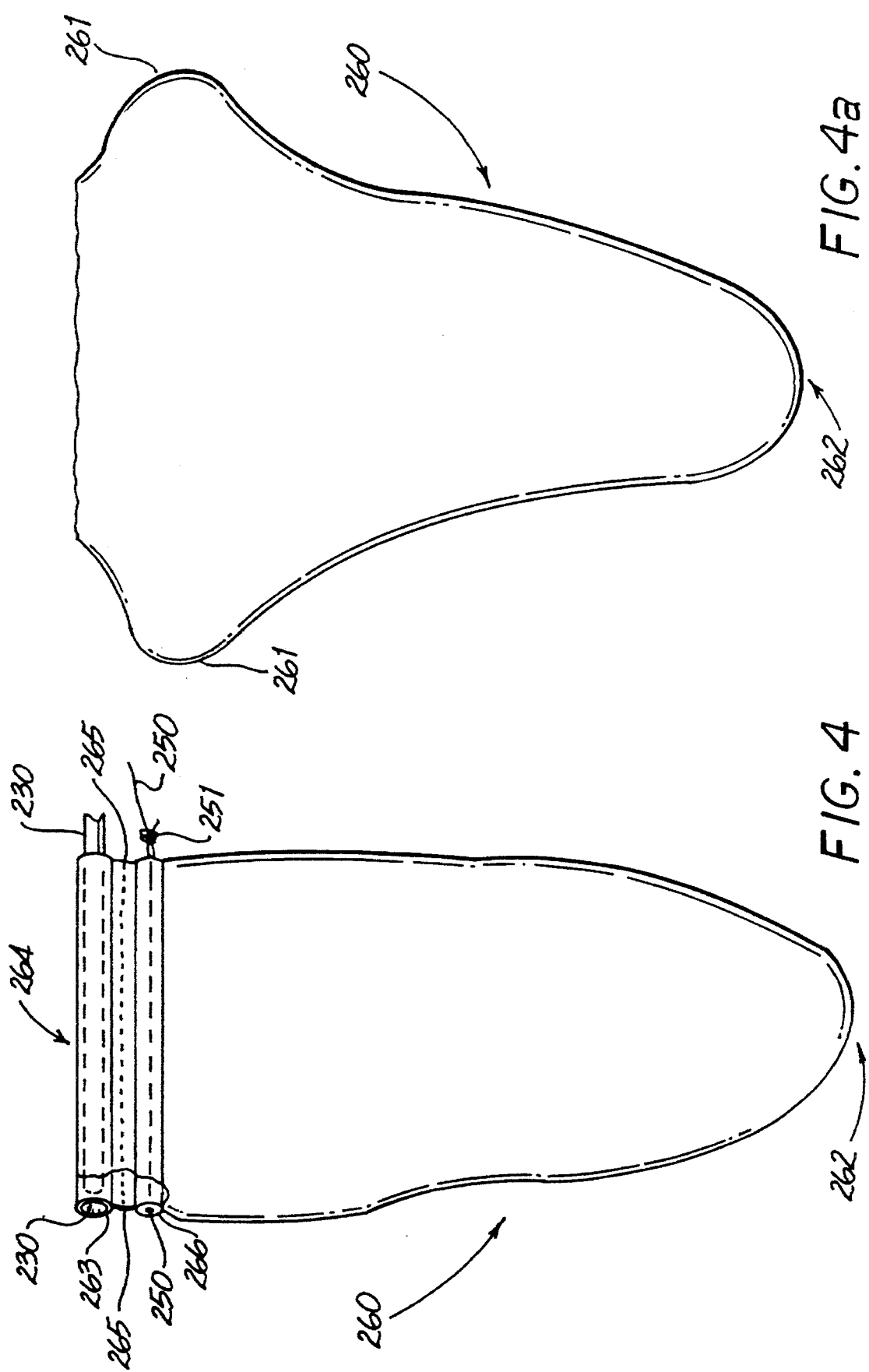

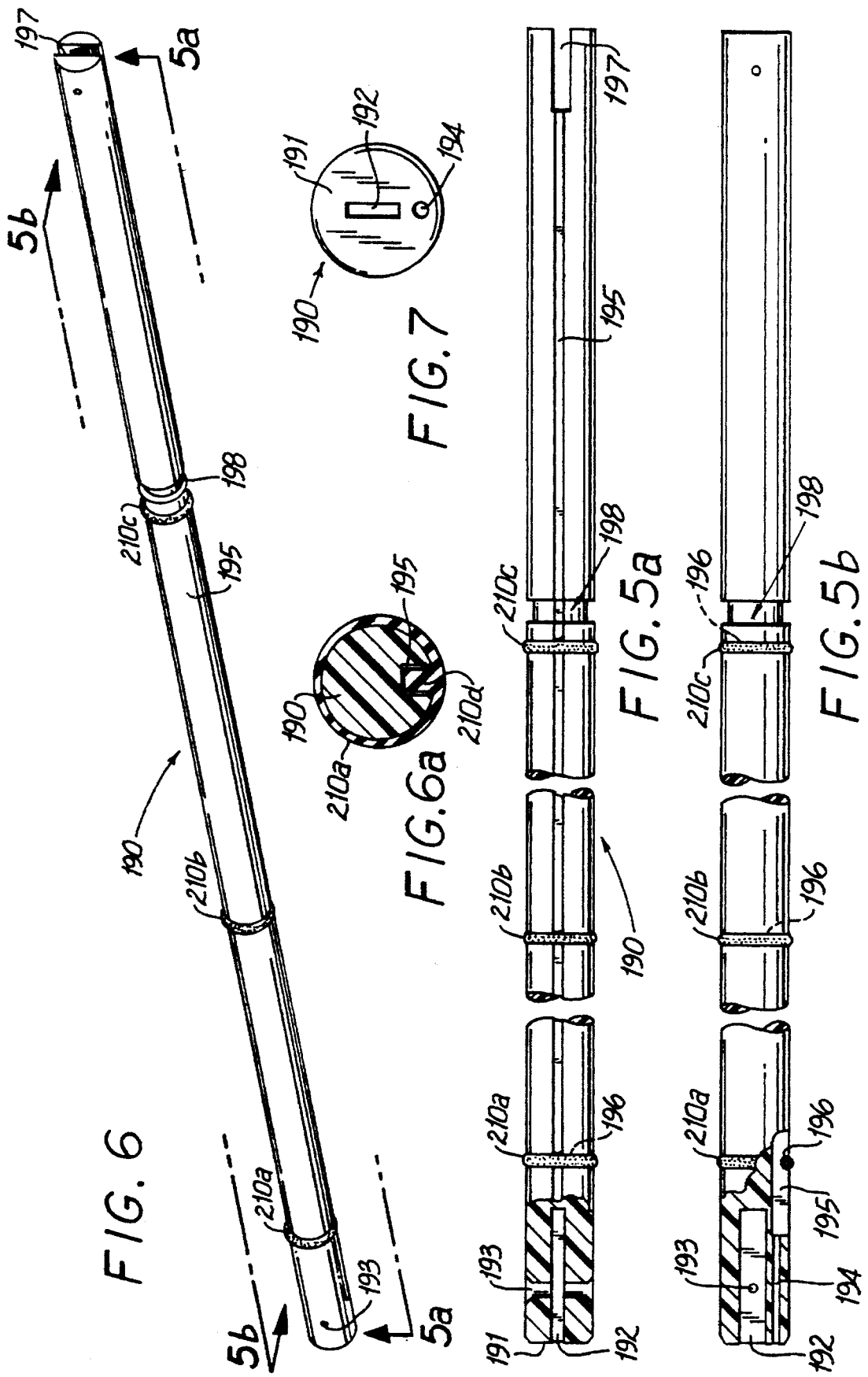

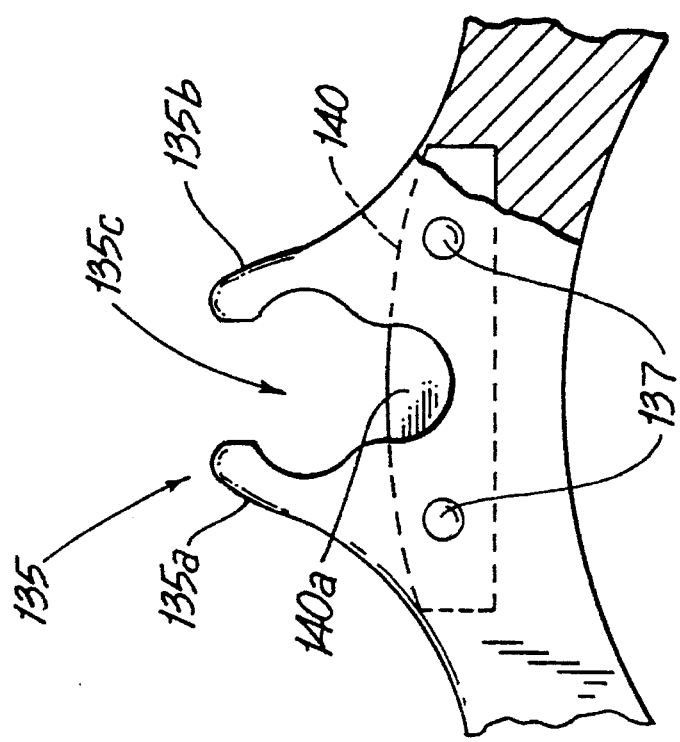
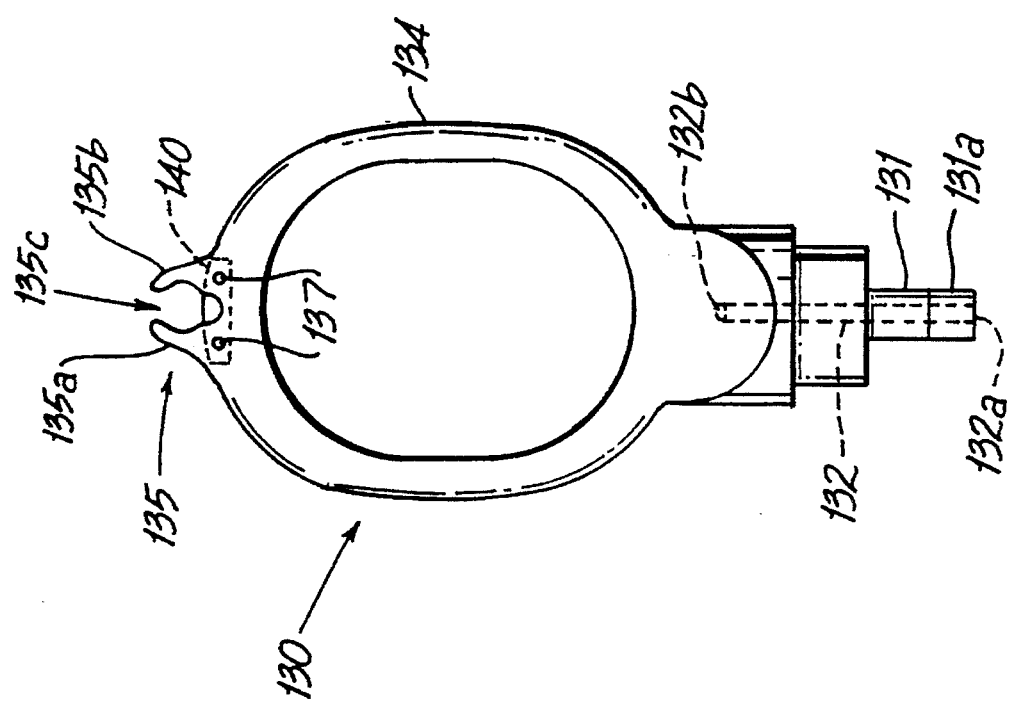

SPECIMEN RETRIEVAL POUCH AND METHOD FOR USE

This application is a continuation-in-part of commonly assigned, U.S. application Ser. No. 07/906,794 filed Jun. 30, 1992, now abandoned.

BACKGROUND OF THE INVENTION

1. Field of the Invention

The present invention relates to a surgical containment apparatus and method for use. More particularly, the present invention relates to a specimen retrieval pouch and method for its use in minimally invasive surgical procedures.

2. Background of the Art

Laparoscopic and endoscopic surgical procedures are minimally invasive procedures in which operations are carried out within the body by means of elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. Laparoscopic and endoscopic procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with means provided to convert longitudinal movement to lateral movement where necessary. Because the endoscopic or laparoscopic tubes, instrumentation, and any required punctures or incisions are relatively narrow, endoscopic or laparoscopic surgery is less invasive and causes much less trauma to the patient as compared to procedures in which the surgeon is required to cut open large areas of body tissue.

Minimally invasive procedures are often used to partially or totally remove body tissue or organs from the interior of the body, e.g. nephrectomy, cholecystectomy and other such procedures. During such procedures, it is common that a cyst, tumor or other affected tissue or organ must be removed via the access opening in the skin, or through a cannula. Various types of entrapment devices have been disclosed to facilitate this procedure.

For example, U.S. Pat. No. 5,037,379 to Clayman et al. discloses a surgical tissue bag for percutaneously debulking tissue by morcellation. The bag includes a layer of puncture-resistant material, a layer of moisture-resistant material and a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is debulked and suctioned out of the bag.

U.S. Pat. No. 5,074,867 to Wilk discloses a planar membrane having filaments attached to its corners. The membrane is placed within a body cavity with the filaments extending through the trocar cannula to the outside of the body. The organ or tissue to be removed is placed on the membrane and the filaments are pulled to close the membrane around the organ and draw it through the cannula, if the organ is sufficiently deformable. If the organ is not sufficiently deformable, e.g. because of the presence of gall stones, a forceps or other instrument is used to crush the stones or tissue.

Although entrapment bags such as those described above are known, there remains a need for an improved specimen retrieval pouch to facilitate tissue removal in minimally invasive surgical procedures.

SUMMARY OF THE INVENTION

Provided herein is an apparatus for removing body tissue from the interior of the body in a minimally invasive surgical procedure. The apparatus includes a pouch having an openable end. The pouch is preferably part of a pouch assembly comprising the pouch and a pouch support. The pouch support can be attached to the drive means. The pouch may have perforations to facilitate detachment of the pouch from the support. The detachment can be simultaneous with the closing of the pouch in response to pulling the drawstring thread.

The apparatus may further include a drawstring thread forming a running loop disposed circumferentially around the pouch in proximity to the openable end thereof; attachment means for slidably attaching a first end portion of the drawstring thread to a second end portion of the drawstring thread to form the running loop; an endoscopic tubular portion having a distal end for insertion into a body; drive means for moving the pouch (i.e., pushing or pulling the pouch) through the endoscopic tubular portion; and stop means having an aperture for permitting passage therethrough of a single thread, the second end portion of the drawstring thread extending through the aperture, and the aperture means possessing a surface for abutting and holding the attachment means.

The pouch can be fabricated from a material selected from the group consisting of polyurethane and latex and preferably is transparent. A running knot is the preferred attachment means.

Stop means is provided by a distal surface of the drive means. The drive means can be an elongated rod slidably disposed within the tubular portion. In the embodiment described below having only a single drawstring thread the aperture of the stop means has a diameter of large enough dimension to permit passage therethrough of only a single threadline, but smaller dimension than the attachment means. The aperture can be oriented parallel to the longitudinal axis of the drive rod or transverse to the longitudinal axis of the drive rod.

The apparatus can further include means for resiliently opening the openable end of the pouch, such as spring means circumferentially attached to the openable end of the pouch and movable between an elongated and narrow closed configuration and a rounded open configuration, the spring means being resiliently biased to the open configuration. The spring means, which can support the pouch as well as open it, is attached to the distal end of the drive means and is slidably movable through the tubular portion when in the closed configuration, and resiliently moveable to its open configuration when moved outside said tubular portion. The spring means can include two elastic prongs each having a proximal end portion having a side surface in facing relation to the side surface of the proximal end portion of the other elastic prong and fastened thereto, and each elastic prong further having a distal end portion joined to the distal end portion of the other prong by a flexible membrane, such as shrink-wrap type tubing, attached to both said end portions.

The pouch can have perforations extending circumferentially therearound between the locations of the spring means and the drawstring thread.

The apparatus preferably further includes at least one gaseous sealing means, such as a coating of viscous sealing material applied to the outer surfaces of the drive means and the drawstring thread, and/or elastomeric seals, for example, o-rings.

Knife means may be provided to cut the drawstring thread.

The apparatus may be fabricated from materials which are gamma stable, thereby permitting gamma sterilization of the instrument.

In use, the apparatus is inserted through a cannula which has been inserted into a body. The pouch is deployed by advancing the drive means. The body tissue is severed, if necessary, and placed within the pouch. The pouch is then closed and detached from the apparatus. The neck of the pouch can then be brought to the distal end of the trocar cannula and the whole assembly removed. Alternatively, after closing and detaching the pouch the pouch can be moved adjacent the interior wall of the patient's body, the apparatus and trocar cannula are then removed, and the neck of the pouch is pulled through an opening in the wall of the body tissue. The bag can then be opened and the specimen, which is still entrapped in the distal end of the pouch in the interior of the patient, can be removed by the surgeon. After removal of the specimen, the pouch may be removed through the same opening in the wall of the body tissue. If later removal of the pouch containing the specimen of body tissue is desired, the pouch and specimen may be "parked" by permitting it to remain in the body cavity until a later time during the operation whereupon the pouch may be removed in conjunction with the same cannula, an alternative cannula, or through an opening in the wall of body tissue in any of the ways discussed.

BRIEF DESCRIPTION OF THE DRAWINGS

Preferred embodiments of the invention are described hereinbelow with reference to the drawings wherein:

FIGS. 3a and 3b illustrate, respectively, in perspective view a running knot, and, as an alternative, an eyelet means for slidably attaching a first end portion of the drawstring thread to a second end portion for form a running loop.

FIG. 4 is an elevational partially cut away view of the specimen removal pouch assembly;

FIG. 4a is an elevational view of an alternative pouch having a circumferential flared section;

FIGS. 5a, 5b, 6 and 7 are, respectively, plan, elevational, perspective, and end views of the drive rod;

FIG. 6a illustrates a side view of O-ring 210a;

FIG. 8 is a bottom plan view of the finger loop;

FIG. 9 is a detached view of the fixture at the proximal end of the finger loop;

DETAILED DESCRIPTION OF PREFERRED EMBODIMENT(S)

As used herein with reference to the present invention, the terms "laparoscopic" and "endoscopic" are interchangeable and refer to instruments having a relatively narrow operating portion for insertion into a cannula or a small incision in the skin, or to a surgical procedure in which such instruments are employed. Use herein of the term "laparoscopic" should not be construed so as to exclude "endoscopic" and use herein of the term "endoscopic" should not be construed so as to exclude "laparoscopic". To the contrary, it is believed that the present invention may find use in any procedure where access to the interior of the body is limited to a relatively small incision, with or without the use of a cannula, including, but not limited to, laparoscopic procedures.

A preferred embodiment of the removal pouch and applicator assembly 100 of the present invention is shown in FIGS. 1 to 9.

Figure 4B:
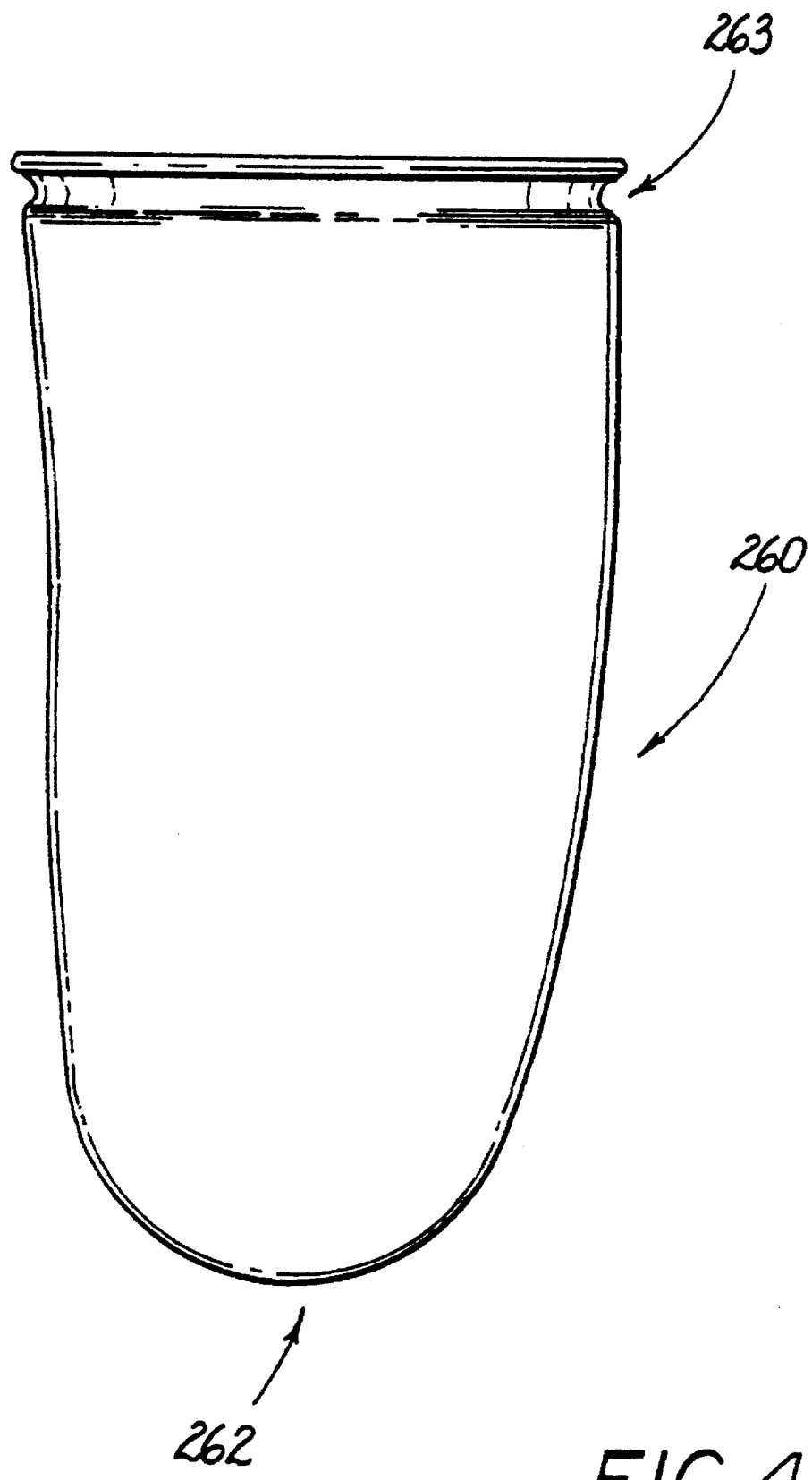
FIG. 4b is an elevational view of an alternative pouch having a proximal, circumferential notch section.

Referring specifically to FIG. 4, the removal pouch 260 includes a flexible film or sheet preferably formed from a substantially transparent polymeric material. A preferred material is polyurethane sheet of about 0.001 to about 0.005 inches in thickness, although other biocompatible materials capable of forming a flexible membrane, such as, for example, latex, may be used, and other appropriate thicknesses. Preferably, the material is transparent to permit viewing of its contents. Also, the pouch material should be impervious to penetration by cancer cells.

The pouch may be of any dimensions suitable for the purpose of organ entrapment or removal. In the present embodiment, the pouch 260 has a diameter of from about 1.5 inches to about 6.0 inches, a depth of from about 2 inches to about 10 inches, and is able to withstand a cubic capacity of up to about 2.0 liters of water, depending upon the pouch's dimensions.

Pouch 260 includes a closed distal end portion 262 and an openable and closable end portion or mouth 264. Optionally, as illustrated in FIG. 4a, the pouch 260 may include a circumferential wider diameter flared portion 261 in the vicinity of the open proximal end portion or mouth 264. The pouch 260 may alternatively include a circumferential concave portion 263 in the vicinity of the open proximal end portion or mouth 264, for facilitating rolling and placement of the pouch 260 within an elongated tube 180 (See FIG. 2). The open proximal end portion or mouth 264 is defined by a proximal (upper) circumferential tubular portion or sleeve 263, and a distal (lower) circumferential tubular portion or sleeve 266, which are spaced apart from each other.

The pouch possesses a linear portion weakened by perforation or, more preferably, scoring, which extends circumferentially around the mouth 264 of the pouch between the proximal and distal sleeves 263 and 266, respectively. The scored line 265 may be created by induction heating to create a linear portion having thickness less than that of the original material to facilitate tearing of the material along the scored line 265.

The proximal sleeve 263 is adapted to receive a spring member 230, described below. The distal sleeve 266 is adapted to receive a drawstring 250. The scored portion 265 is adapted to tear when the drawstring 250 is pulled with sufficient force so as to close the mouth 264 of the bag distal to the perforation 265, thereby providing fast detachment of pouch 260 from the spring member 230 simultaneously with closure of mouth 264. Clearly, alternative means also can be utilized to detach the pouch 260 from the spring member 230, such as by pulling with a grasper or by cutting with a scissors.

Referring now to FIGS. 1a, 1b, 2 and 3, the laparoscopic removal pouch and applicator assembly includes the elongated tube 180 which is of such dimensions so as to be insertable through a trocar cannula for endoscopic or laparoscopic procedures.

Figure 1:
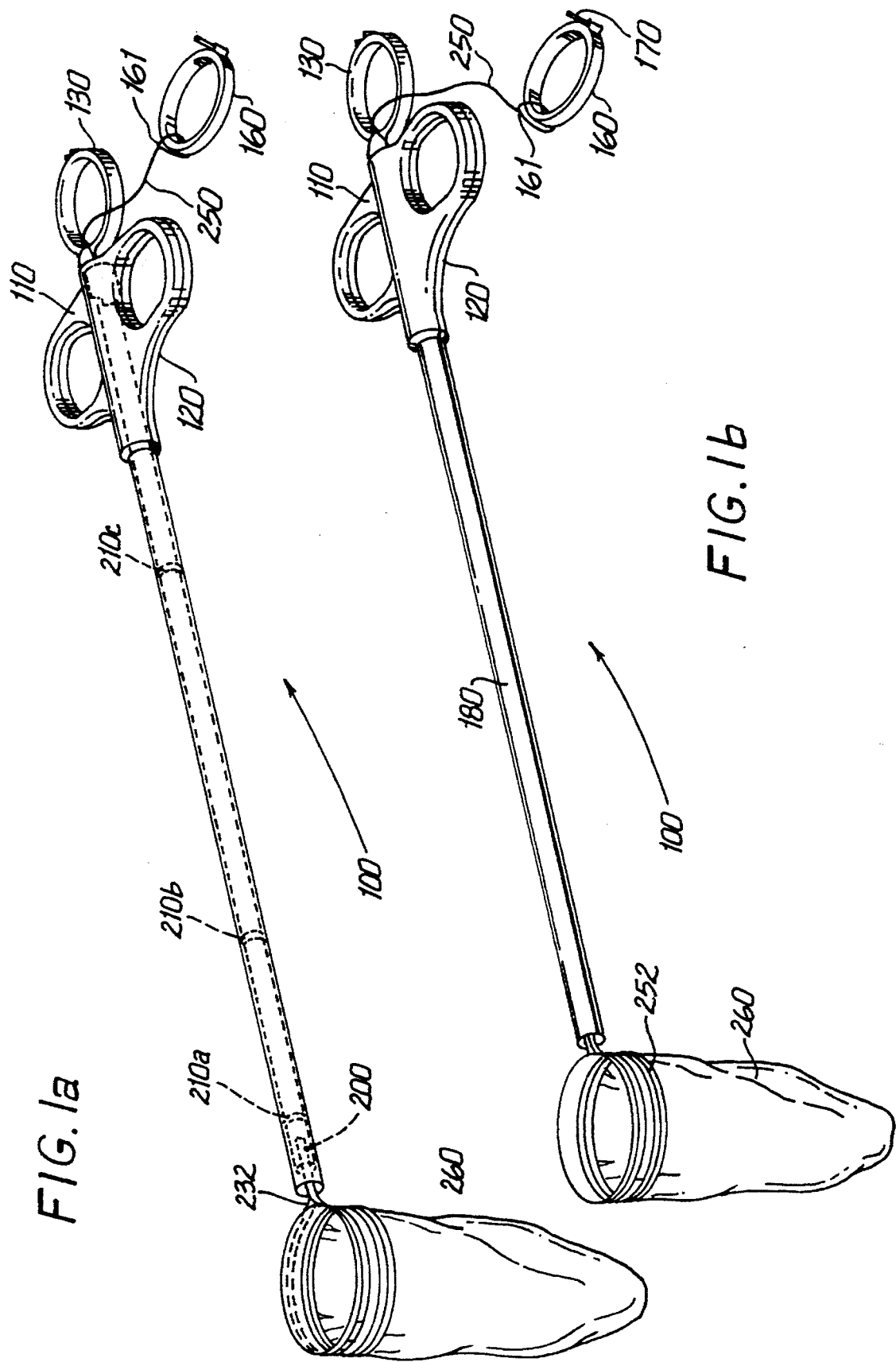
FIGS. 1a and 1b are perspective views of the apparatus of the present invention in the deployed configuration.
Figure 2:
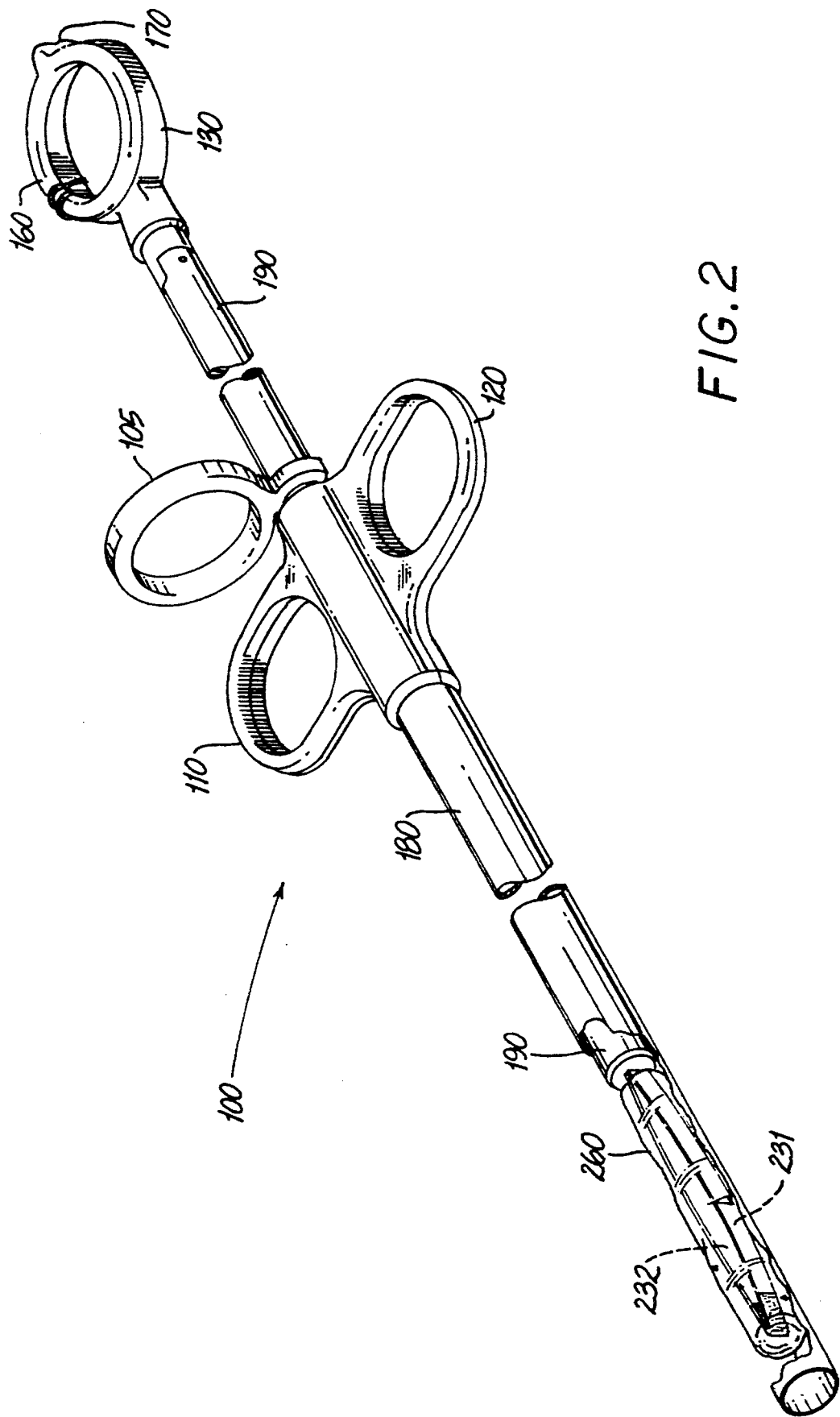
FIG. 2 is a perspective view of the apparatus in the initial, undeployed configuration.
Figure 16:
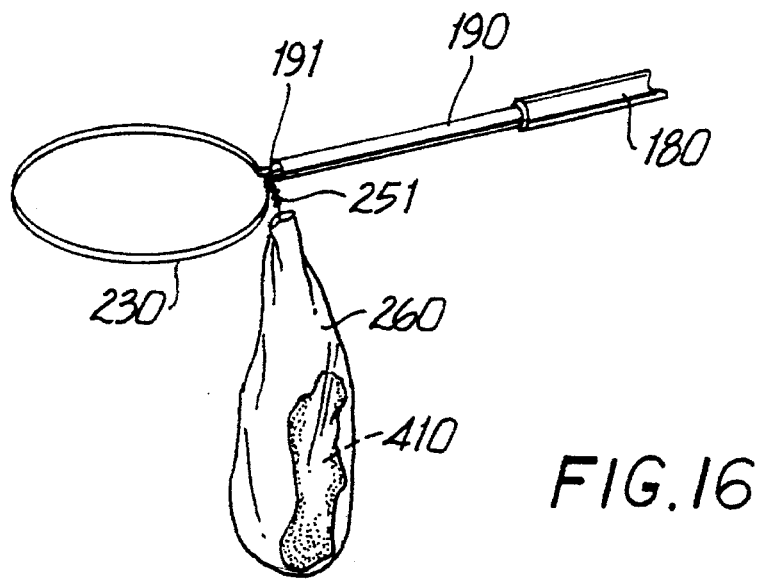

Referring additionally now to FIGS. 5, 6 and 7, the drive rod or bar is an elongated generally cylindrical member slidably disposed through the bore of tube 180. Drive rod 190 includes a distal pushing end 191 and is attached to the pouch assembly to move the pouch from a non-deployed position contained within the outer tube 180 (as shown in FIG. 2) to a deployed position distal to the outer tube 180, (as shown in FIGS. 1a and 16). A spring retainer slot 192 extends longitudinally through the drive rod and opens at the distal end 191. Aperture 193 extends transverse to the drive rod 190 across the spring retainer slot 192. Pin 200 is disposed through aperture 193 and through apertures 231b and 232b (See FIGS. 3, 5a and 5b) for fastening spring 230 within retainer slot 192.

Drawstring aperture 194 extends longitudinally through the drive rod opening distally at end 192. Drawstring aperture 194 opens proximally into drawstring slot 195, which extends longitudinally along the drive rod 190. Drawstring slot 195 terminates at its proximal end at slot 197. Proximal slot 197 is adapted to receive finger loop 130. Drive rod 190 also includes circumferential slots 196 for receiving O-rings 210a, 210b and 210c. The O-rings help maintain a gaseous seal and/or help to maintain the drawstring in place while permitting sliding movement of the drive rod 190 through tube 180. As shown in FIG. 6a, O-ring 210a includes an inwardly pointing projection 210d for providing additional fluid and gas sealability.

The drive rod 190 is preferably fabricated from a strong polymeric material. A material suitable for fabricating the drive rod 190 is polycarbonate plastic with 20% glass fiber filler. If gamma sterilization is desired, this material has the additional advantage of being gamma stable. Other materials suitable for the purposes discussed herein may also be used. To maintain a gaseous seal within the instrument, close tolerances are observed. The outer diameter of the drive rod 190 is slightly less than the inner diameter of the tube 180 through which it slides longitudinally. Additionally, the drive rod 190 is preferably coated with grease as a viscous sealing material to insure that no gases exit or enter the body through the seal when the operation site (e.g. the peritoneum or other body cavity) is insufflated. Any grease that will operate as a viscous sealing material may be used, but if gamma sterilization is desired the grease chosen should be gamma stable. A material suitable for viscous sealing which is also gamma stable is Antiseize Thread Compound 767 available from the Loctite Corporation. A locking tab 105 is included to prevent premature actuation of the instrument during shipping. The locking tab includes snap fit engagement means to engage slot 198 of the drive rod. When thus engaged, the drive rod cannot be pushed distally beyond the point where the locking tab 105 engages the proximal end of the handle portions 110, 120. To actuate the instrument the surgeon must first disengage the locking tab by pulling it off the instrument.

The spring 230 comprises two flexible and resilient strips 231 and 232 which, in unstressed or freely expanded condition together form a generally circular hoop for supporting the periphery of opening 264 of pouch 260. Each strip 231 and 232 has a proximal end portion, 231a and 232a, respectively, with apertures 231b and 232b extending laterally therethrough. The proximal end portions 231a and 232a are adapted to be received into slot 192 of the drive rod 190 so that longitudinal movement of the drive rod 190 in the manner described below will move spring 230 and attached pouch 260. Apertures 231b and 232b are configured so as to align with aperture 193 of the drive rod, thereby permitting disposition therethrough of pin 200. The distal ends 231c and 232c, respectively, meet in opposing relationship where they are joined by tubing 240 made from polymeric, and preferably shrink-wrap type material. In addition, a plurality of arrows 241 may be disposed about the tubing 240 to aid in the manufacturing assembly of the instrument and to also help the surgeon properly orientate the pouch 260, prior to organ entrapment and removal. Spring 230 is preferably fabricated from a resilient metal. One example of such a resilient metal is stainless steel. Other resilient materials are also contemplated, including TINEL brand super elastic metal available from Raychem Corporation of Menlo Park, Calif. and plastic.

Figure 3:
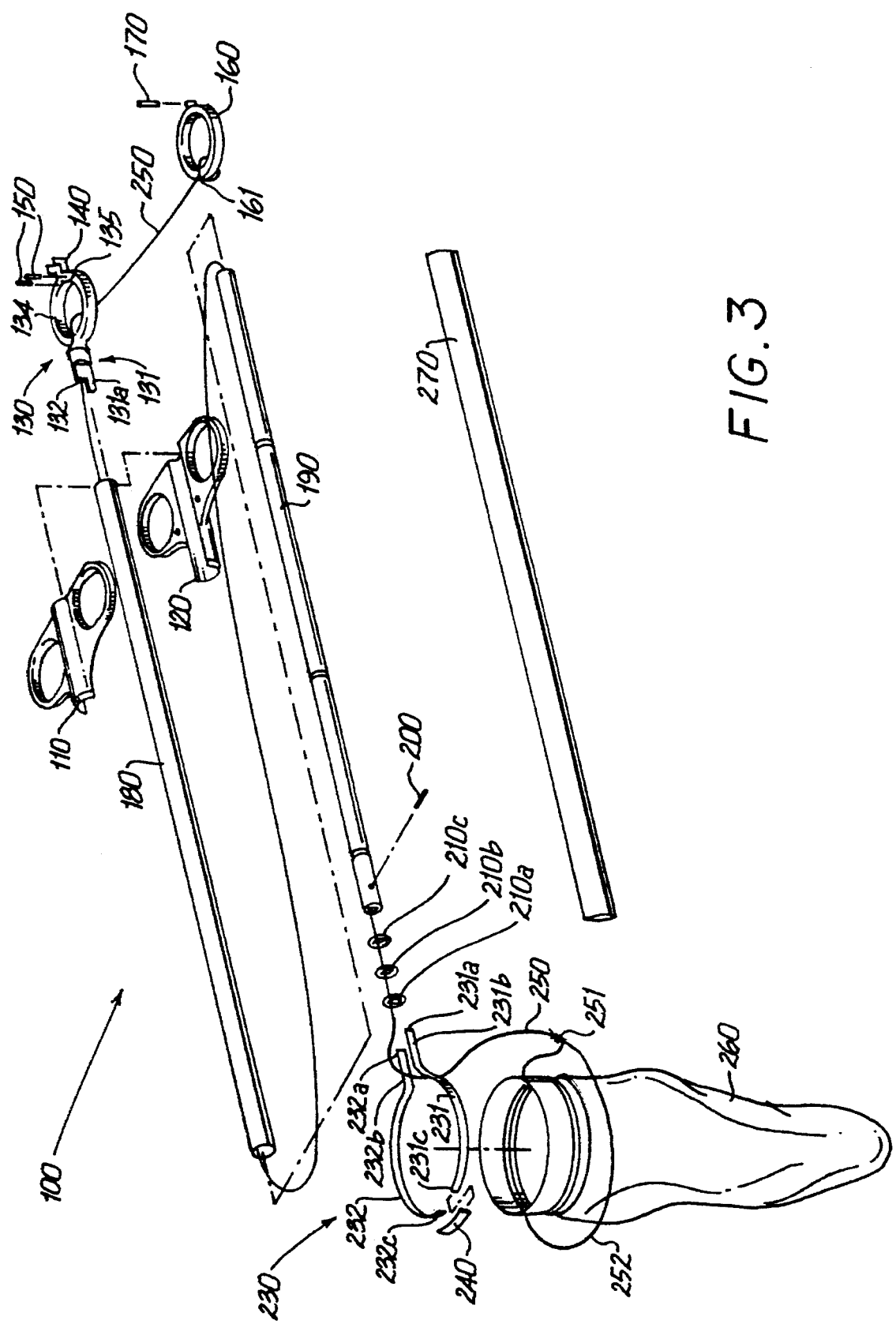
FIG. 3 is an exploded perspective view of the apparatus.
Figure 8A:
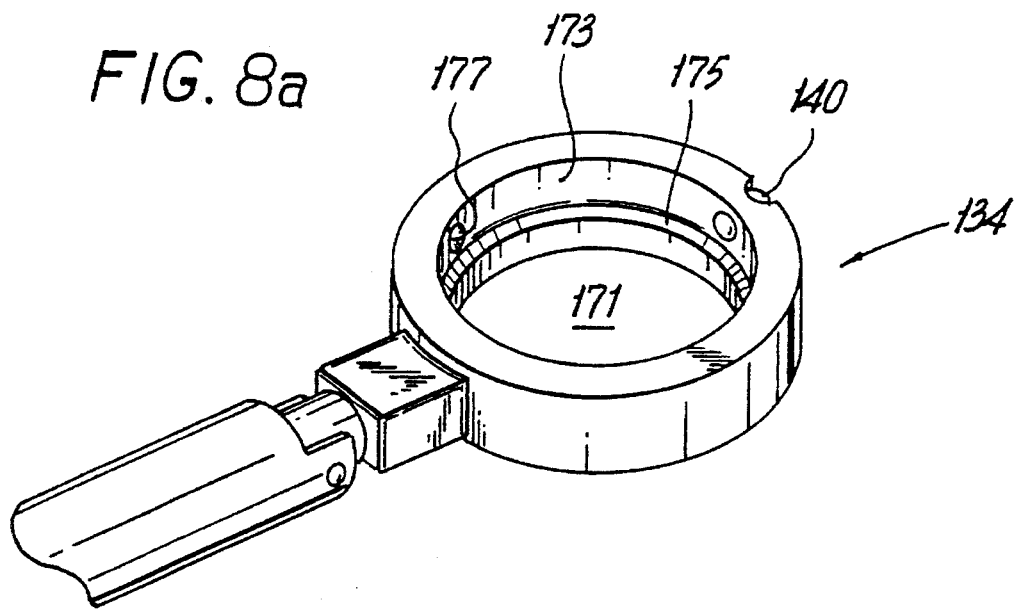
FIGS. 8a and 8b are perspective views of alternative finger loops.
Figure 8B:
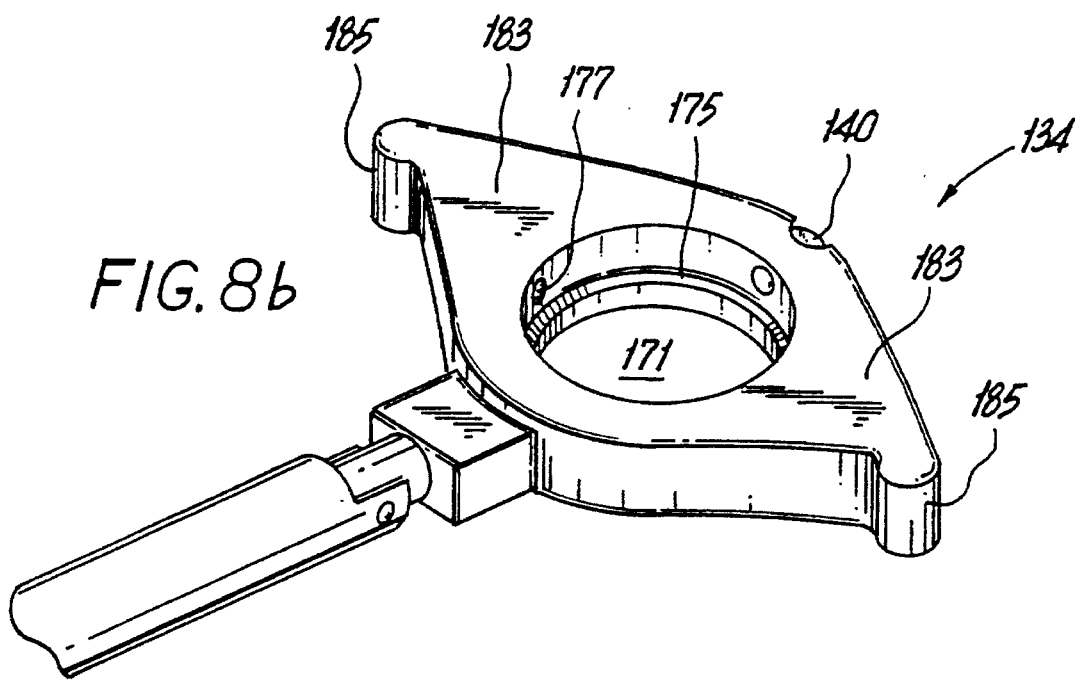
Figure 8C:
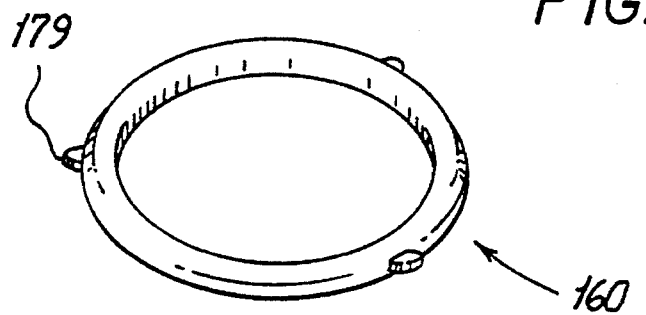
FIG. 8c is a perspective view of a pull ring for engagement with the alternative finger loop.

Referring now to FIGS. 3, 8 and 9, the finger loop 130 includes a ring portion 134 for engagement by a user's finger. The distal end of the finger loop includes projection 131 for engaging slot 197 in the drive rod 190, wherein the projection 132 is fixedly attached. Projection 131 includes a key portion 131a which engages a corresponding notch in the handle portion 120 to prevent relative rotation of the drive rod within the apparatus when the pouch is fully deployed. Aperture 132 extends longitudinally from distal opening 132a to proximal opening 132b. Aperture 132 receives thread 250. At its proximal end, finger loop 130 may possess a fixture 135 for releasably holding pull ring 160. Fixture 135 comprises spaced apart generally proximally pointing prongs 135a and 135b which define a proximally opening mouth 135c for snap-fit reception of post 170 of the pull ring 160. In an alternate embodiment shown in FIG. 8a, ring portion 134 has an interior recess 171 dimensioned to releasably hold pull ring 160 (FIG. 8c). Interior recess 171 is defined by interior wall 173 of ring portion 134 and shoulder 175. The interior wall 173 contains at least one depression 177, for snap-fit reception of corresponding projections 179 of pull ring 160. In the preferred embodiment, three circumferential depressions 177 are disposed along the interior wall 173, one at a distal end thereof and two opposite each other at a proximal end thereof. As seen in FIG. 8b, ring portion 134 may also include projections 183 to allow the instrument to be gripped with more than one finger, if desired. In the preferred embodiment, projections 183 extend outwardly in a transverse direction from ring portion 160 and include tapered ends 185. Tapered ends 185 may be rounded and may also include a slight bend to facilitate gripping with more than one finger, when desired. Knife 140 is mounted laterally across the mouth at the distal end thereof with sharp knife edge 140a pointed proximally. The knife blade 140 is secured at the fixture 135 by means of pins 150 disposed through apertures 137 in the finger loop 130. The knife edge 140a functions to cut the drawstring 250, as will be described below. Alternatively, the knife can be insert molded or mounted, onto the finger loop 130.

Referring to FIG. 3, handle portions 110 and 120 are fixedly joined together to form a unitary ring handle, which is fixedly mounted to the proximal end of tube 180 for receipt of a user's finger to facilitate manipulation of the instrument.

Pull ring 160 is a finger ring to facilitate pulling of drawstring 250 to which it is attached, preferably by means of an adhesive. In one embodiment, post 170, which may be in integral part of pull ring 160, is pivotally mounted into mouth 135c of fixture 135 in a snap-fit engagement and may be disengaged by exerting a pulling force thereon to separate ring 160 from ring portion 134 for reasons discussed below. When utilizing post 170, pull ring 160 preferably includes projection 161 which is engageable with a corresponding depression in finger loop 130 to prevent inadvertent or unintended pivoting of the pull ring 160. In an alternate embodiment, FIG. 8b, pull ring 160 includes at least one projection 179 for snap-fit engagement with corresponding depressions 177 of ring portion 134 and may be disengaged by exerting a pulling or pushing force sufficient to separate pull ring 160 from ring portion 134 for reasons discussed below. In a preferred embodiment, the pull ring is distinctively colored to alert the user as to the orientation of the pouch 260.

Drawstring 250 is tied at one end to pull ring 160, and extends through aperture 132 in the finger loop, through drawstring slot 195 in the drive rod, through drawstring aperture 194, and around the mouth 264 of the pouch through lower tubular chamber 266. The drawstring is preferably coated with grease as a viscous sealing material to insure that gases do not enter or exit the peritoneum through aperture 194. Any grease that will operate as a viscous sealing material may be used, but if gamma sterilization is desired the grease chosen should be gamma stable. As previously mentioned, a material suitable for viscous sealing which is also gamma stable is Antiseize Thread Compound 767 available from the Loctite Corporation. The end of the drawstring is brought around and tied to the drawstring to form a loop 252 tied by knot 251. Knot 251 is a "running knot", i.e. a knot that slips along the rope or line around which it is tied. Thus, loop 252 tightens when the standing part of the line is pulled. For proper operation, knot 251 should have a size larger than the diameter of aperture 194. When drawstring 250 is pulled proximally, the knot 251 will be pulled up to the distal opening of aperture 194 where the knot 251 will abut the distal face 191 of drive rod 190. Aperture 194 has a diameter large enough to admit a single threadline of drawstring 250 with minimal clearance to help maintain a gaseous seal with further sealing provided by the grease, but not large enough to permit knot 251 to pass through. Thus, knot 251 is retained in position while drawstring 250 is pulled proximally, thereby closing loop 252. This, in turn, closes mouth 264 of pouch 260 and detaches the lower portion of pouch 260 along perforation 265. Use of the running knot enables closing and opening of the pouch to be achieved by a single actuating line of drawstring thread moving through the apparatus. An aperture or thread passage in a laparoscopic instrument for accommodating a single line of thread need not have as large a diameter as that for accommodating two or more lines of drawstring thread.

A further advantage is that it is easier to maintain a proper gaseous seal within aperture 194 when a single thread is moved therethrough than if two or more lines of thread were disposed therethrough. Although apparatus configurations having only a single actuating threadline are preferred, also contemplated as being within the scope of the present invention are apparatus employing multiple actuating threadlines from, for example, two or more threads, or doubled-over single threads.

Any type of running knot having the proper diameter may be used, such as the slip knot or running bowline, and variations thereof. The knot preferably should maintain enough friction on the drawstring such that the knot slides along the drawstring when the drawstring is pulled with sufficient tension. The knot should also preferably slide in both a distal and proximal direction for closing, and if necessary to facilitate removal of tissue, opening of the pouch after detachment.

The present invention contemplates means other than knots for accomplishing the same function as described above. For example, rings, eyelets, and the like may be used. As shown in FIG. 3A, one end of the drawstring thread is attached to ring member 220, which has an aperture 221 for receiving drawstring 250. When the drawstring 250 is pulled proximally, ring member 220 abuts the proximal face 181 at aperture 194, permitting drawstring 250 to be pulled through, thereby closing loop 252.

Thus, any means for slidably attaching one end of the drawstring to the drawstring thread to form a reducible loop, or running noose, is contemplated as being within the scope of the present invention.

Tube 180 is of such diameter as to permit it to be slidably disposed through a trocar cannula for use in endoscopic or laparoscopic operations, and is generally between about 0.25 inches to 0.50 inches in diameter, and about 10 inches to about 15 inches long, although other dimensions may also be used if appropriate to the operation being performed. Tube 180 slidably houses the drive rod 190 and, when undeployed, the spring 230 and pouch 260. In the initial, unused condition, pouch 260 will be rolled up and spring portions 231 and 232 will be relatively straight and positioned within tube 180. When the drive rod 190 is advanced, the spring 230 connected thereto will exit the distal end of tube 180 and resiliently pop open, thereby deploying and opening pouch 260. Tube 180 is preferably from a metal such as stainless steel and is preferably coated with a shrink wrap plastic such as shrinkable polyethylene fiberglass, or polyvinyl chloride of a grade suitable for use in surgical procedures.

METHOD(S)

Introduction

Minimally invasive surgery in the abdomen usually requires the placement of one or more trocar assemblies in the abdominal wall to provide access to the peritoneum for the surgical instruments. The trocar assembly may include an obturator with a sharp, tissue piercing point, a cannula having a tube and a proximal section which usually includes valve and sealing means. The surgeon inserts the trocar assembly into the abdominal wall and then removes the obturator leaving the cannula inserted into the body cavity and the proximal section outside the body. The body cavity is then insufflated. Additional cannulas can be inserted and various operating and optical viewing instruments may be inserted through the several cannulas. The cannula sealing means helps prevent the entry or escape of gas between the inside of the cannula and the outside of the instrument. As mentioned before, the instruments generally have internal sealing means to prevent the escape or entry of gas through the interior of the instrument. Placement of trocar cannulas and insertion of instruments therethrough are performed in accordance with methods and apparatus known and commonly available to those with skill in the art.

Method of the Present Invention

Referring now to FIGS. 10 to 20, a method of using the apparatus of the present invention in minimally invasive surgery will now be described. By way of illustration, surgical procedures in which the method of the present invention may be used include, but are not limited to, nephrectomy, cholecystectomy, appendectomy, and the like.

Figure 10:
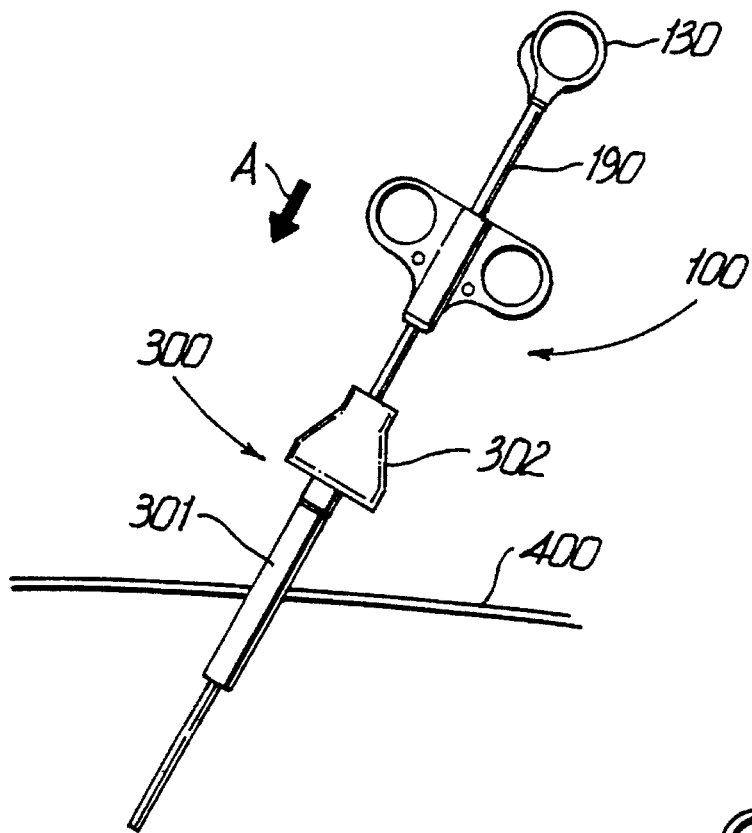
FIG. 10 illustrates the insertion of the apparatus of the present invention through a trocar cannula into a body cavity.

FIG. 10 shows a diagrammatic view of a trocar cannula 300 inserted through a wall of body tissue 400 to gain access to a body cavity, such as for example the peritoneum. The applicator assembly 100, with the specimen retrieval pouch in the non-deployed position is inserted through the cannula 300 in the direction of arrow A such that the distal end of the applicator assembly 100 is positioned within the body cavity. As depicted in FIG. 10, the applicator assembly is in the initial condition with specimen retrieval pouch 260 retained within tube 180. Pull ring 160 is positioned atop post 170. The locking tab 105 is removed at this time to permit actuation of the instrument.

Figure 11:
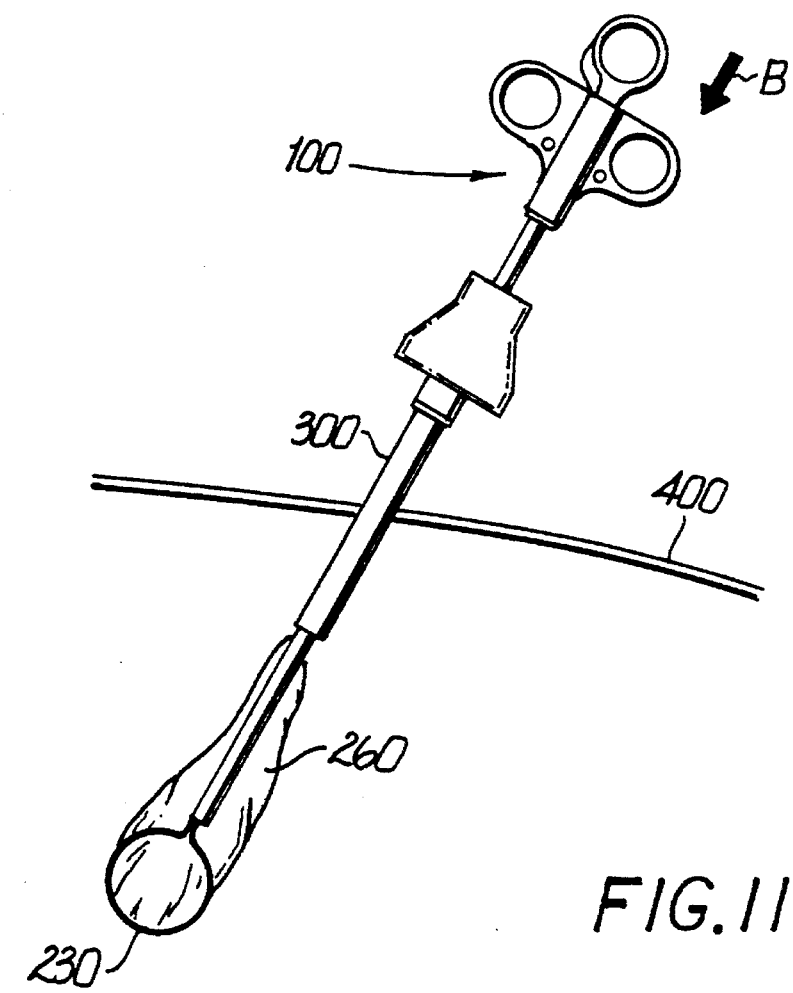
FIGS. 11 and 12 illustrate deployment of the specimen removal pouch.

Referring now to FIG. 11, the drive rod 190 is advanced longitudinally distally by the surgeon's pushing of the finger loop 130 as indicated by arrow B. The finger loops of ring portion 110 (and 120) may be grasped by the user during the movement of finger loop 130. This movement, of drive rod 190 advances the pouch 260 beyond the distal end of tube 180 where spring 230 is no longer restrained by tube 180 and, therefore, resiliently pops open to its substantially round configuration to thereby open the mouth 264 of the pouch.

Figure 12:
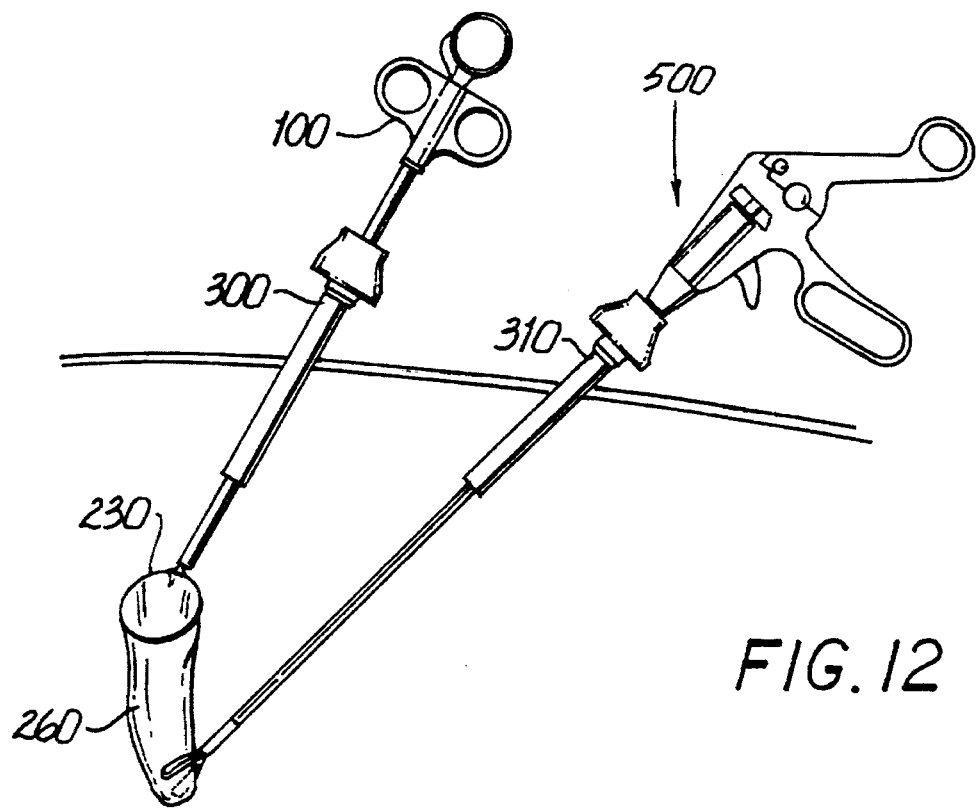

Referring now to FIG. 12, non-traumatic forceps or graspers 500 may be inserted through another cannula and manipulated to gently unroll the pouch 260 if necessary.

Figure 13:
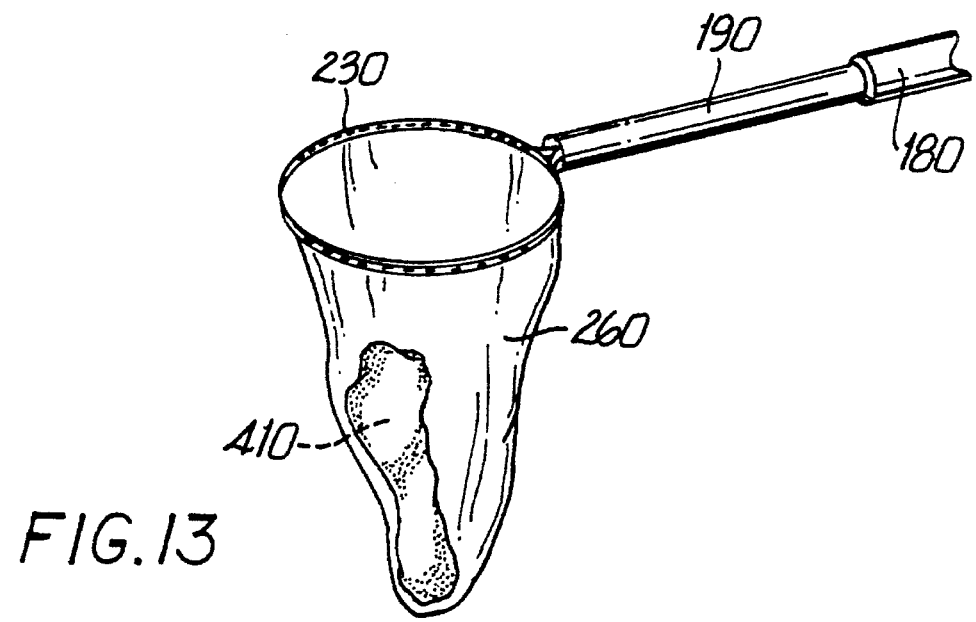
FIG. 13 illustrates the entrapment of a tissue specimen.

Referring to FIG. 13, the specimen of body tissue 410 is excised and placed into pouch 260. The specimen may optionally be treated, i.e. morcellated or otherwise divided prior to removal from the body cavity.

Figure 15:
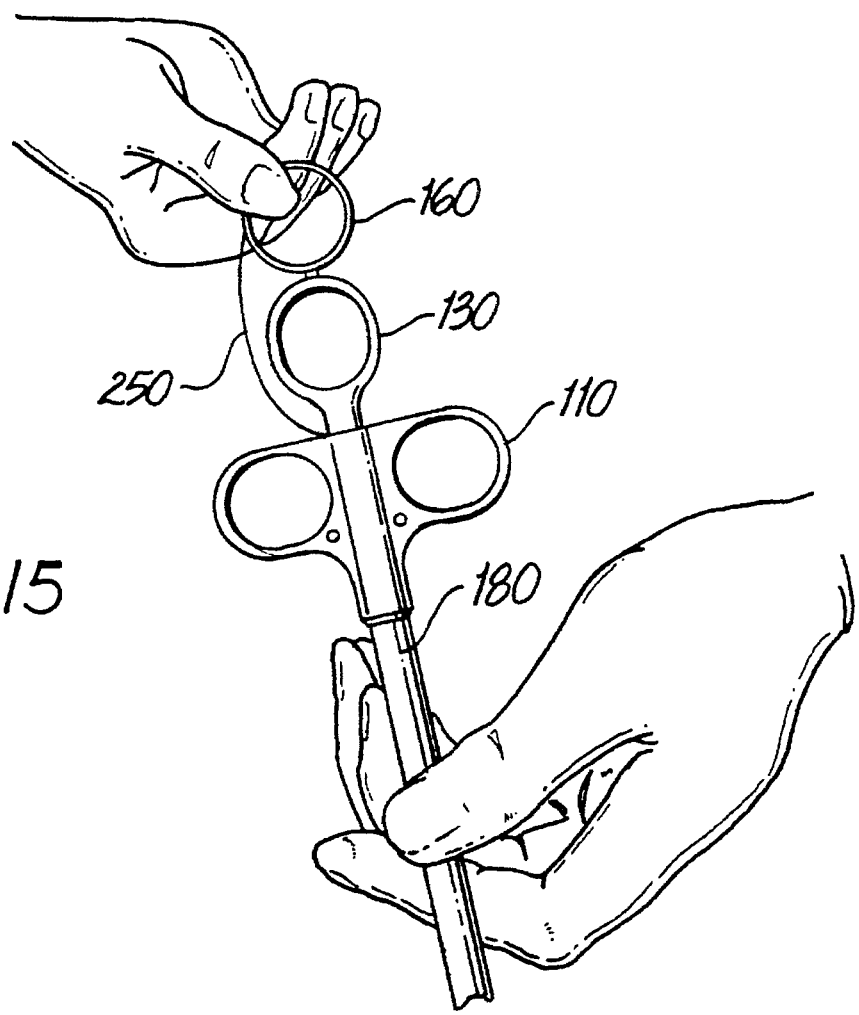
FIGS. 14, 15 and 16 illustrate closure of the pouch.
Figure 14:
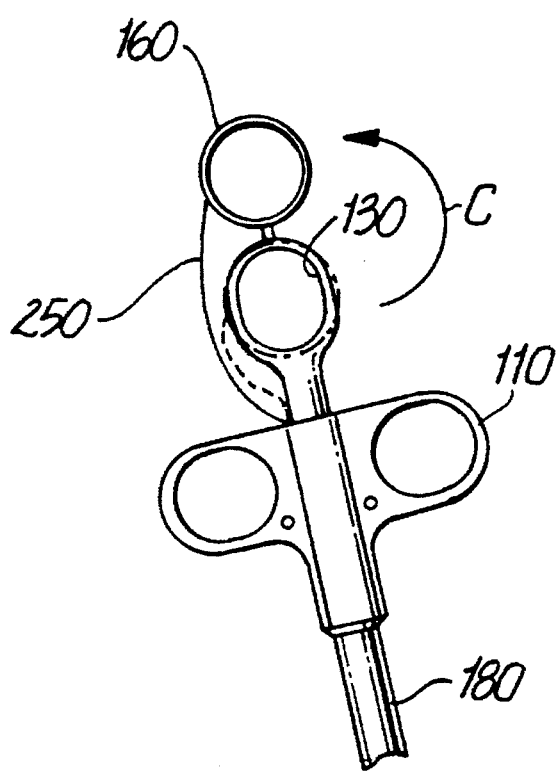

Referring to FIG. 14, the pull ring 160 is pivoted with post 170 in a direction as shown by arrow C to a position as illustrated in FIG. 15.

Referring to FIG. 15, the pull ring 160 is grasped and pulled thereby disengaging post 170 from fixture 135 and permitting removal of pull ring 160 from the finger loop 130.

When the pull ring 160 is pulled (FIG. 16), drawstring 250 is moved proximally, thereby detaching the pouch 260 from the spring support 230 along perforation line 265. Continued pulling of the drawstring 250 will bring running knot 251 into abutment with the distal end 191 of the pusher thus reducing noose or loop 252 and closing the mouth of the pouch 260.

Figure 17:
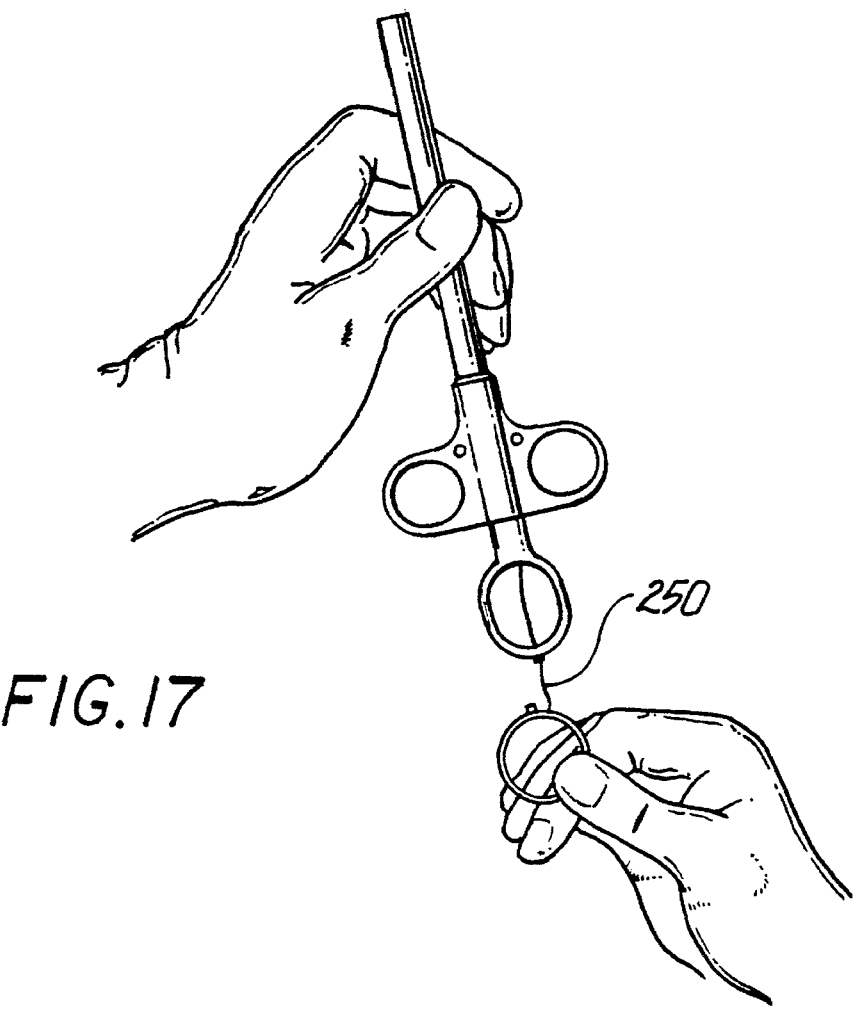
FIG. 17 illustrates cutting of the drawstring.

Referring to FIG. 17, the drawstring 250 is inserted into mouth 135c of fixture 135 and cut by knife 140 to allow for subsequent removal of the instrument with the closed pouch remaining inside the body cavity.

Figure 18:
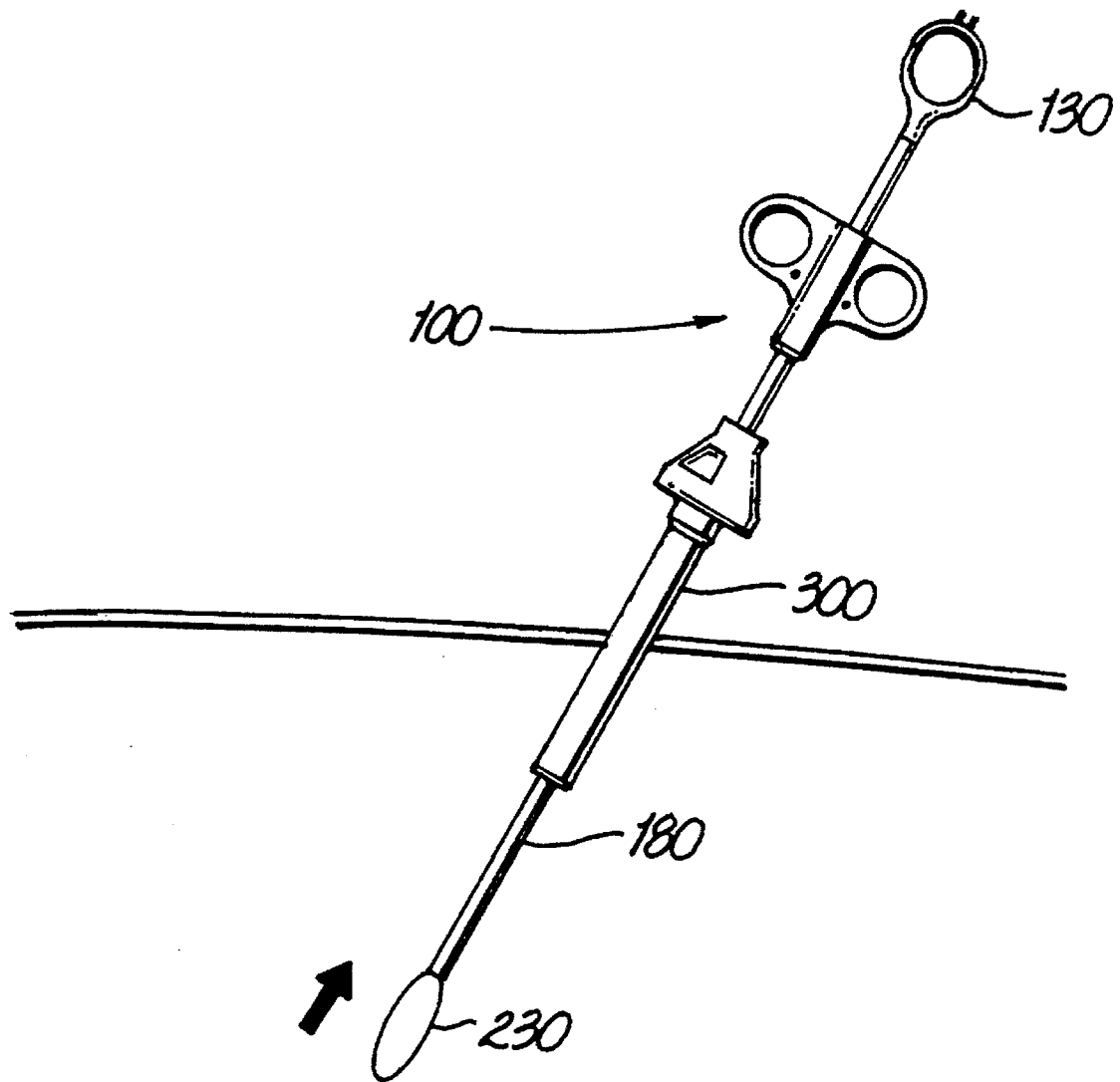
FIG. 18 illustrates removal of the apparatus from the cannula.

Referring to FIG. 18 the finger loop 130 is pulled so as to withdraw spring 230 back into tube 180, whereupon spring 230 refolds back into its predeployed relatively straight configuration to permit removal of the apparatus 100 from the cannula 300. The drive rod 190 is not retracted completely out of the proximal end of tube 180, since complete retraction of the drive rod will permit exit of the spring 230 and subsequent opening of the spring 230 outside the proximal end of the apparatus.

Figure 19:
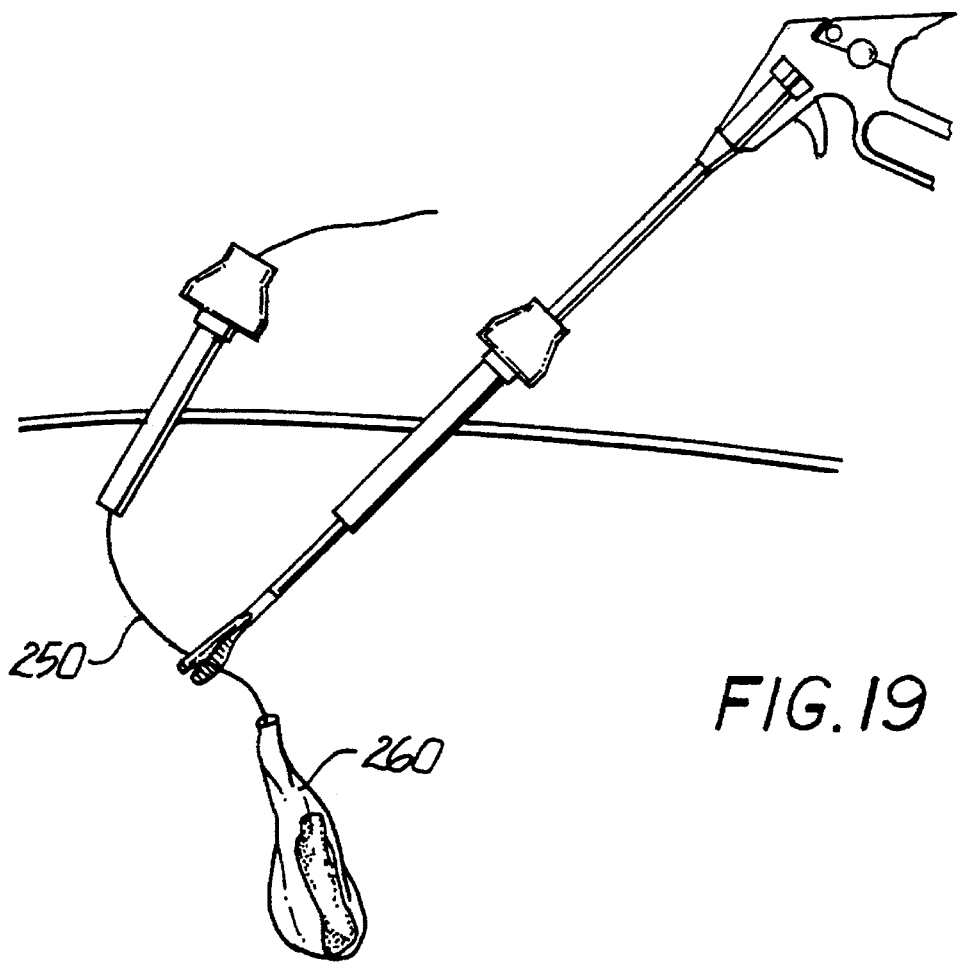
FIGS. 19 and 20 illustrate follow-up procedures for removal of the pouch.
Figure 20:
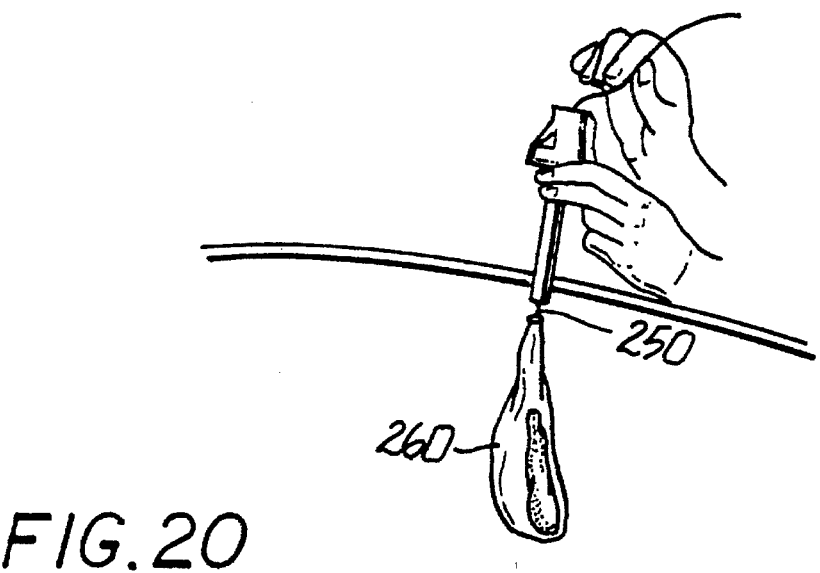

At this point drawstring 250 is sitting in the cannula and as shown in FIG. 20, the pouch with tissue specimen can be immediately removed through the trocar site by pulling the drawstring 250 through the cannula until the end of the pouch 260 reaches the neck of the trocar and both can be removed together, or the trocar can be removed first and removed thereafter through the same incision. Alternatively, with the drawstring securely holding the pouch closed, the drawstring may be grasped by an appropriate endoscopic instrument, such as a grasper, and held inside the body cavity, as shown in FIG. 19, and removed at a later time during the operation. If necessary, the incision may be enlarged to permit passage therethrough of the pouch and specimen. However, it is alternatively contemplated that if the specimens contained in the pouch is sufficiently small, or if divided as discussed above, it can be removed through the cannula.

ALTERNATIVE EMBODIMENT

Figure 21:
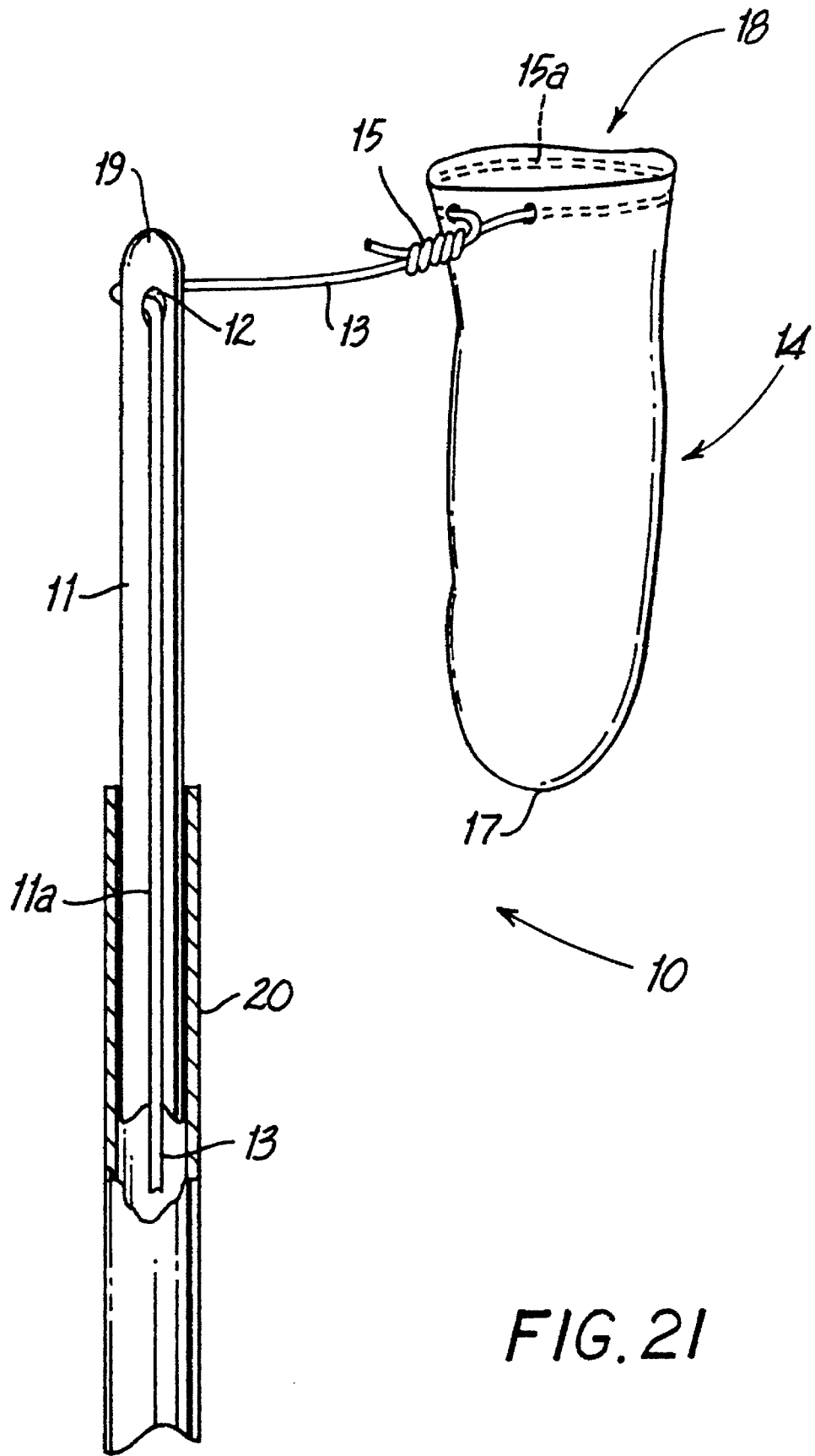
FIG. 21 illustrates an alternative embodiment in a partially cutaway view.

FIG. 21 illustrates an alternative embodiment of a laparoscopic removal pouch assembly 10. The flexible removal pouch 14 has a closed distal end 17 and an open proximal end 18. The pouch is preferably fabricated from a latex or other material suitable for use in surgical procedures. A drawstring 13 is disposed laterally through transverse aperture 12 in proximity to the distal end of the push rod 11. Push rod 11 is an elongated member having a blunt end 19 for pushing pouch 14 through a cannula 20. Preferably, push rod 11 has a longitudinal slot 11a through which the drawstring thread 13 may be disposed. The drawstring 13 is disposed around the open end 18 of the pouch 14 to form a loop in a sewn-in type construction 16, whereupon it terminates in a running knot 15 to form running noose 15a. The aperture 12 has a diameter large enough to admit drawstring 13, but not large enough to permit running knot 15 to pass through.

In use, the blunt end 19 of the push rod 11 is used to push the inner surface of closed end 17 to insert pouch 14 through a cannula inserted through an opening in a tissue wall into a body cavity. The pouch 14 is removed from the rod 11 by means of a grasper inserted through another cannula and positioned in proximity to the tissue severed for removal. The pouch 14 is manipulated so as to scoop up the tissue into the closed end 17, and the drawstring 13 is then pulled from outside the body to cinch closed the open end 18 of the pouch 14. When the drawstring 13 is pulled, knot 15 abuts the rod 11 at aperture 12 and, since knot 15 is too large to pass through, it is stopped from moving further. Continued pulling of drawstring 13 results in closing of the noose 15a and, therefore, closing of the mouth 18 of the pouch. The tissue specimen is thereby trapped within the pouch 14. Rod 11 is then pulled proximally out of the cannula, drawing the pouch 14 and excised body tissue therethrough or through the incision in the wall of the body tissue.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical apparatus for removing body tissue from an interior portion of a body in a minimally invasive surgical procedure, which comprises:

a) an endoscopic portion having a longitudinally extending bore and configured and dimensioned to be at least partially insertable through a cannula;

b) a pouch assembly movable between a proximal location at least partially within said endoscopic portion and a distal location at least partially exterior to said endoscopic portion, said pouch assembly including a support and a pouch removably attached to said support, said pouch having a first end movable between an open configuration and a closed configuration, and a closed second end;

b) a drive member slidably disposed within said bore for moving said pouch from said proximal location to said distal location, said support being attached to a distal end of said drive member;

c) means associated with said pouch for detaching said pouch from said support;

d) closing means for moving said first end of said pouch from said open configuration to said closed configuration; and e) gaseous seal means for preventing passage of fluid or gases through said apparatus.

2. The apparatus of claim 1, wherein said pouch includes a circumferential concave portion adjacent said first end for facilitating rolling and placing of said pouch within said tubular member.

3. The apparatus of claim 1, further comprising means for properly orienting said pouch, said means for properly orienting said pouch being disposed about said pouch.

4. The apparatus of claim 3, wherein said means for properly orienting said pouch comprises a plurality of opaque arrows printed on said support.

5. The apparatus of claim 1, wherein said closing means comprises a drawstring thread, said drawstring thread having a first end portion slidably attached to a second end portion of said drawstring thread thereby forming a running loop.

6. The apparatus of claim 5, wherein said running loop comprises a running bowline, said running bowline being slidable in both a distal and a proximal direction for both closing and opening said pouch.

7. The apparatus of claim 5, wherein said running loop comprises a slip knot, said slip knot being slidable in both a distal and a proximal direction for both closing and opening said pouch.

8. The apparatus of claim 5 further comprising grasping means located at a proximal end of said drive member for permitting actuation of said drive member by a user.

9. The apparatus of claim 8, wherein said grasping means comprises a drive rod pull ring.

10. The apparatus of claim 9, wherein said drive rod pull ring includes at least one projection for gripping of said pull ring with at least one finger.

11. The apparatus of claim 9 further including a drawstring pull ring attached to said drawstring at one end.

12. The apparatus of claim 11, wherein said drive rod pull ring includes a recess, and said drawstring pull ring is removably mounted within said recess.

13. The apparatus of claim 12 further including a knife mounted to said drive rod pull ring.

14. The apparatus of claim 1, wherein said pouch is dimensioned to withstand a cubic capacity from about 15 liters to about 2.0 liters.

15. The apparatus of claim 13, wherein said pouch is fabricated from a material selected from the group consisting of polyurethane and latex.

16. The apparatus of claim 13, wherein said pouch is fabricated from transparent material which is substantially impervious to the passage therethrough of cancer cells.

17. The apparatus of claim 1, wherein said surgical apparatus is fabricated from gamma stable material.

18. The apparatus of claim 1, wherein said means associated with said pouch comprises at least one perforation formed in said pouch, adjacent said first end.

19. The apparatus of claim 1, wherein said means associated with said pouch comprises a line of perforations extending circumferentially around said pouch, adjacent said first end.

20. A surgical apparatus for removing tissue from an interior portion of a body during a surgical procedure which comprises:

a) an elongated tube having a longitudinally extending bore extending therethrough;

b) a pouch assembly movable between a first position at least partially disposed within the bore and a second position at least partially exterior to the bore, the pouch assembly including:

a support member and a pouch removably attached to the support member, the pouch having a first end biased into an open configuration by the support member and movable between the open configuration and a closed configuration, and a closed second end;

c) a drive member slidably disposed within the bore for moving the pouch from the first position to the second position, the support member being attached to the drive member at one end; and d) a closing member operatively associated with the pouch, wherein actuation of the closing member moves the first end of the pouch from the open configuration to the closed configuration while detaching the pouch from the support member.

21. The surgical apparatus according to claim 20 wherein the closing member comprises a drawstring thread, the drawstring thread having a first end portion slidably attached to a second end portion of the drawstring thread thereby forming a running knot.

22. The surgical apparatus according to claim 21 wherein the running knot is in abutment with the drive member.

* * * * *